(12) United States Patent
Van Der Mooren et al.

(10) Patent No.: US 10,159,565 B2
(45) Date of Patent: Dec. 25, 2018

(54) APPARATUS, SYSTEM AND METHOD TO ACCOUNT FOR SPHERICAL ABERRATION AT THE IRIS PLANE IN THE DESIGN OF AN INTRAOCULAR LENS

(71) Applicant: AMO Groningen B.V., Groningen (NL)

(72) Inventors: Marrie H Van Der Mooren, Groningen (NL); Patricia Ann Piers, Groningen (NL); Theophilus Bogaert, Groningen (NL); Sverker Norrby, Leek (NL); Carmen Canovas-Vidal, Groningen (NL)

(73) Assignee: AMO Groningen B.V., Groningen (NL)

( * ) Notice: Subject to any disclaimer, the term of this patent is extended or adjusted under 35 U.S.C. 154(b) by 0 days.

(21) Appl. No.: 13/651,611

(22) Filed: Oct. 15, 2012

(65) Prior Publication Data
US 2013/0282116 A1    Oct. 24, 2013

Related U.S. Application Data

(60) Provisional application No. 61/547,454, filed on Oct. 14, 2011, provisional application No. 61/642,649, filed on May 4, 2012.

(51) Int. Cl.
*A61F 2/16*        (2006.01)
*A61B 3/10*        (2006.01)
(Continued)

(52) U.S. Cl.
CPC .......... *A61F 2/1637* (2013.01); *A61B 3/0025* (2013.01); *A61B 3/1005* (2013.01);
(Continued)

(58) Field of Classification Search
CPC ........ A61F 2/1637; A61F 2/1613; A61F 2/16; A61F 2240/002; G02C 7/024; A61B 3/1005
(Continued)

(56) References Cited

U.S. PATENT DOCUMENTS

2009/0281552 A1    11/2009    Hiramatsu et al.
2012/0158132 A1*    6/2012    Canovas Vidal .... A61B 3/0025
                                                                    623/6.43

FOREIGN PATENT DOCUMENTS

WO          06053216 A2    5/2006
WO       2010035139 A2    4/2010
(Continued)

OTHER PUBLICATIONS

International Search Report and Written Opinion for Application No. PCT/EP2012/070381, dated Jan. 17, 2013, 13 pages.
(Continued)

*Primary Examiner* — Howie Matthews
(74) *Attorney, Agent, or Firm* — Johnson & Johnson Surgical Vision, Inc.

(57) ABSTRACT

An intraocular lens, and a system and method of customizing at least one characteristic for an intraocular lens, in accordance with a regression that indicates the postoperative spherical aberration at the iris plane of a patient aphakic eye, in order to obtain a desired postoperative condition. The lens, system and method of customizing at least one characteristic of an intraocular lens may include measuring at least one biometric parameter of an eye at a desired light level, determining a desired postoperative condition of the eye, obtaining a corneal spherical aberration and an anterior chamber depth of the eye, and empirically calculating a spherical aberration at an iris or pupil plane of the eye, based on a regression formula comprising at least the corneal spherical aberration and the anterior chamber depth, and cross products thereof.

4 Claims, 13 Drawing Sheets

(51) Int. Cl.
*A61B 3/00* (2006.01)
*G02C 7/02* (2006.01)

(52) U.S. Cl.
CPC .............. *A61F 2/16* (2013.01); *G02C 7/024* (2013.01); *A61F 2240/002* (2013.01)

(58) Field of Classification Search
USPC ....................................................... 623/6.11
See application file for complete search history.

(56) References Cited

FOREIGN PATENT DOCUMENTS

| | | |
|---|---|---|
| WO | 2011100544 A1 | 8/2011 |
| WO | 2012082898 A1 | 6/2012 |

OTHER PUBLICATIONS

Olsen T., et al., "Intraocular Lens Power Calculation with an Improved Anterior Chamber Depth Prediction Algorithm," Journal of Cataract & Refractive Surgery, 1995, vol. 21 (3), pp. 313-319.

\* cited by examiner

APPARATUS, SYSTEM AND METHOD TO ACCOUNT FOR SPHERICAL ABERRATION AT THE IRIS PLANE IN THE DESIGN OF AN INTRAOCULAR LENS

CROSS-REFERENCES TO RELATED APPLICATIONS

This patent application claims priority to U.S. provisional patent application 61/547,454 filed on Oct. 14, 2011 and U.S. provisional patent application 61/642,649 filed on May 4, 2012, the entire contents of both of which are incorporated herein by reference for all purposes as if fully set forth herein.

FIELD OF THE INVENTION

The present invention relates generally to the design of intraocular lenses (IOLs) and, more particularly, is directed to an apparatus, system and method to account for spherical aberration at the iris plane in the design and selection of an intraocular lens.

BACKGROUND OF THE INVENTION

Intraocular Lenses (IOLs) are frequently used for restoring or improving visual performance, such as after cataract surgery. Because an IOL may be selected from various providers and with differing IOL characteristics, reliable systems and methods to select IOLs having IOL characteristics that achieve the desired refractive outcome for a patient, such as in terms of spectacle correction and/or image quality, are needed. More particularly, it is typically desirable to select an IOL that will substantially achieve emmetropia for the patient after surgery, independent of the refractive state of the patient prior to implantation. The term emmetropia, and variations thereof, is used herein to indicate a state of vision in which an object at infinite distance from the subject eye is in sharp focus with the eye's lens in a neutral state.

The IOL characteristics necessary to achieve emmetropia are often calculated using empirical regressions. For example, the Saunders, Retzlaff, and Kraff formula (SRK) is a regression formula empirically derived from clinical data to indicate the optimal power for an IOL. The SRK regression formula is:

$$P = A - 2.5 * AXL - 0.9 * K$$

where P is the IOL power, A is the lens constant, AXL is the axial length in millimeters, and K is the average corneal curvature in diopters. Unfortunately, the SRK regression formula may yield inadequate indications, which has led to the development of the SRKII and SRK/T formulae.

More particularly, in the SRK/T method, the calculation is partially based on a previous regression analysis to predict the position of the IOL in the eye after surgery. Once the position is known, the IOL power to implant is calculated by simple paraxial optics, taking into account that the eye is a two lens system (wherein the two lenses are the cornea and the IOL), focusing on the retina. This approach is based on Fyodorov's theoretical formula.

There are numerous other formulae for calculating IOL characteristics, such as the Haigis, Hoffer Q, Olsen, and Holladay 1 and 2 models, for example. An in-depth analysis of IOL power calculation methods is provided in Shammas H J (ed.), *Intraocular Lens Power Calculations*, Thorofare, N.J.; Slack (2004).

Current power calculation procedures are paraxial and by definition do not account for spherical aberration present in cornea and IOL. Ray tracing procedures include wavefront aberrations but this is not a common tool in current clinical practice.

Various IOLs are designed to correct for either no corneal spherical aberration, or, at best, for the average corneal spherical aberration, present in a cataract population. Further, these IOL lenses, whether designed to correct for no corneal spherical aberration or the average corneal spherical aberration, are typically designed based solely on the average distance between the cornea and the implanted IOL. However, it is well understood that, in a typical sample of patients, the corneal spherical aberration may vary well outside the average range, as may the distance between the cornea and the IOL upon implantation. These variations may occur, for example, due to the patient's preoperative state, due to the surgical precision, or due to the healing process likely for a given eye configuration, for example. Available lenses typically do not provide post-operative spherical aberration compensation for patients having non-average eye characteristics prior to implantation. Since the wavefront aberrations change as a wavefront propagates through the eye, a procedure to predict the spherical aberration at the pupil plane creates the possibility to design and to select an IOL to obtain a desired ocular spherical aberration.

Post-lasik eyes are a particular example of eyes that are not "average". For example, the post-lasik eye may have characteristics that are difficult to measure due to the surgical modifications to the eye, and it is well understood that these surgical modifications to the post-lasik eye, such as the decoupling that occurs between the anterior and posterior corneal radius after lasik, make certain of the eye characteristics calculated for "average" patients inaccurate for postlasik eyes. Thus, it is well known that it is exceedingly difficult to provide a recommended IOL having characteristics that will produce the desired refractive outcome and residual ocular spherical aberration for post-lasik patients.

More particularly, for example, it has been widely reported that standard lasik procedure may typically generate large amounts of corneal aberrations. This may be inferred because post-lasik patients typically present higher amounts of corneal aberrations, likely due to the lasik surgery, than would an "average" patient. Such aberrations should not be excluded in the calculation of recommended IOL characteristics if the desired refractive outcome is to be obtained.

Thus, the need exists for an apparatus, system and method for recommending an IOL having characteristics likely to provide an improved visual outcome by accounting for at least the post-operative spherical aberration at the iris plane and that is simpler than ray tracing. This need may be met, for example, by accounting for a particular patient's expected anterior chamber depth (ACD), and more particularly by accounting for a non-average distance between the cornea and the implanted IOL, and/or by additionally considering a particular patient's variation from the average corneal spherical aberration.

BRIEF DESCRIPTION OF THE FIGURES

Embodiments of the present invention will be understood with reference to the detailed description in conjunction with the accompanying figures, in which like numerals indicate like aspects, and wherein.

SUMMARY OF THE INVENTION

Figure 1:
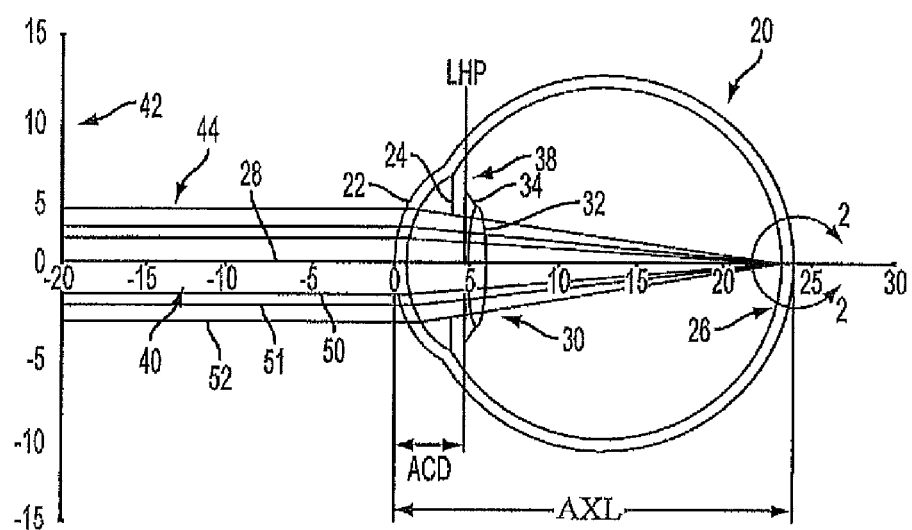
FIG. 1 is a graphical representation of the elements of an eye model used in various embodiments of the present invention.

The present invention includes at least an intraocular lens, and a system and method of customizing or selecting at least one characteristic for an intraocular lens, in accordance with a regression that indicates the postoperative spherical aberration at the iris plane of a patient eye, in order to obtain a desired postoperative condition.

The method of customizing at least one characteristic of an intraocular lens may include measuring at least one biometric parameter of an eye at a desired light level, determining a desired postoperative condition of the eye, obtaining a corneal spherical aberration and an expected post-operative anterior chamber depth of the eye, and calculating a spherical aberration at an iris plane of the eye, based on a model regression formula comprising at least the corneal spherical aberration, corneal power and the post-operative anterior chamber depth, and cross products thereof. The method may further include predictively estimating, in accordance with an output of the empirically calculating and the at least one biometric parameter, the at least one characteristic of the intraocular lens to obtain the desired postoperative condition.

The at least one biometric parameter may be at least one of axial length, and corneal power, and the desired light level may be at 6 millimeters pupil, for example. The desired postoperative condition may comprise a postoperative refraction, or the at least one characteristic of the intraocular lens may be an optical power, for example.

In addition to aspects of the aforementioned method, the system for predicting at least one characteristic of the intraocular lens may include a first computing device capable of measuring at least one biometric parameter of an eye, a second computing device programmed to simulate a corneal spherical aberration and a post-operative anterior chamber depth of the eye according to the at least one biometric parameter, and a third computing device programmed to apply, by at least one computing processor, a regression to the at least one biometric parameter, the corneal spherical aberration, the post-operative anterior chamber depth, and cross products thereof, wherein the regression is of the form:

$SA_r = -0.285451 + 1.00614 * SA_c + 0.0742716 * ACD + 0.0371122 * cor + 0.153398 * SA_c * ACD - 0.0788237 * SA_c * cor - 0.00967978 * cor * ACD$, wherein $SA_r$ is spherical aberration at an iris plane of the aphakic eye, $SA_c$ is the corneal spherical aberration, ACD is the anterior chamber depth, and cor is an anterior corneal radius of the eye.

The system may further include an output from the third computing device, comprising an optimized one of the at least one characteristic to obtain a desired postoperative condition calculated in accordance with the regression. The system may further include a feedback input to the third computing device for modifying the regression in accordance with the optimized one of the at least one characteristic.

In addition to the aspects of the method and system of the present invention, an intraocular lens according to the present invention may include a selected optic from a plurality of available optics, wherein the selected optic may be a selection capable of correcting a spherical aberration at an iris plane of the eye that obeys the equation:

$SA_r = -A + B*SA_c + C*ACD + D*cor + E*SA_c*ACD - F*SA_c*cor - G*cor*ACD$, wherein A, B, C, D, E, F and G are empirically derived constants, $SA_r$ is the spherical aberration at the iris plane, $SA_c$ is corneal spherical aberration of the eye, ACD is a predicted post-operative anterior chamber depth of the eye, and cor is an anterior corneal radius of the eye. The lens may further include at least one haptic for physically supporting the selected optic in situ.

Another preferred method comprises fitting the measured ocular SA to the measured corneal spherical aberration and IOL position or pupil plane. This can be done in order to yield personalized constants.

Therefore, the present invention provides an apparatus, system and method an apparatus, system and method for recommending or designing an IOL having characteristics likely to provide an improved visual outcome by accounting for at least the post-operative spherical aberration at the iris plane. The present invention accounts for anterior chamber depth (ACD), and more particularly accounts for the non-average distance between the cornea and the implanted IOL, and additionally considers variations in corneal spherical aberration outside the average range.

DETAILED DESCRIPTION OF THE EMBODIMENTS

It is to be understood that the figures and descriptions of the present invention have been simplified to illustrate elements that are relevant for a clear understanding of the present invention, while eliminating, for the purpose of clarity and brevity, many other elements found in typical implantable optic apparatuses, systems and methods. Those of ordinary skill in the art may thus recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

The present invention is directed to apparatuses, systems and methods for selecting characteristics, such as optical power, for spherical and aspheric intraocular lenses (IOLs) to provide a predetermined ocular spherical aberration and/ or refractive outcome for "average" and "non-average" patients. Aspects of the invention may be understood with reference to FIG. 1, which is a graphical representation of a model eye 20 having cornea 22, iris 24, retina 26, and optical axis 28. IOL 30 is disposed within eye 20, and IOL 30 may include an optic 32 and one or more haptics 34 having distal ends 38. In general, eye 20 may have the dimensional parameters illustrated by the geometry shown, including the axial length (AXL) and the anterior chamber depth (ACD) of eye 20.

As used herein, the anterior chamber is the space between cornea 22 and front vertex of the IOL. The anterior chamber is filled with the aqueous humor, and communicates through the pupil with the posterior chamber. The span of the anterior chamber is herein defined as the ACD. The average adult eye has an ACD of about 3.15 mm, although the ACD typically shallows by about 0.01 mm per year. Further, the ACD is dependent on the accommodative state of the eye, and is indicative of the accommodative capability of the eye. The range of ACD may vary between 2 mm and 5 mm Other dimensional parameters that may be included in model eye 20 include, but are not limited to, the corneal radius (CR), the corneal power (K) and the crystalline lens thickness (LT). Model eye 20 may also include various other parameters, such as, for example, the refractive indices of the various portions of eye 20 and/or IOL 30.

The illustration of FIG. 1 indicates a coordinate system having a horizontal axis 40 and a vertical axis 42, shown in units of millimeters. FIG. 1 shows a plurality of rays 44 entering the cornea 22 and IOL 33. The plurality of rays 44 comprises a paraxial ray 50 that is disposed near the optical axis 28, and a marginal ray 52 that is disposed near the edge of the opening formed by the iris 24. The plurality of rays 44 additionally comprises an averaged ray 51 disposed between the paraxial ray 50 and the marginal ray 52, for example, at a height, at the pupil, of 1/{square root of (2)} or ½ times the height of the entrance pupil height.

Figure 2:
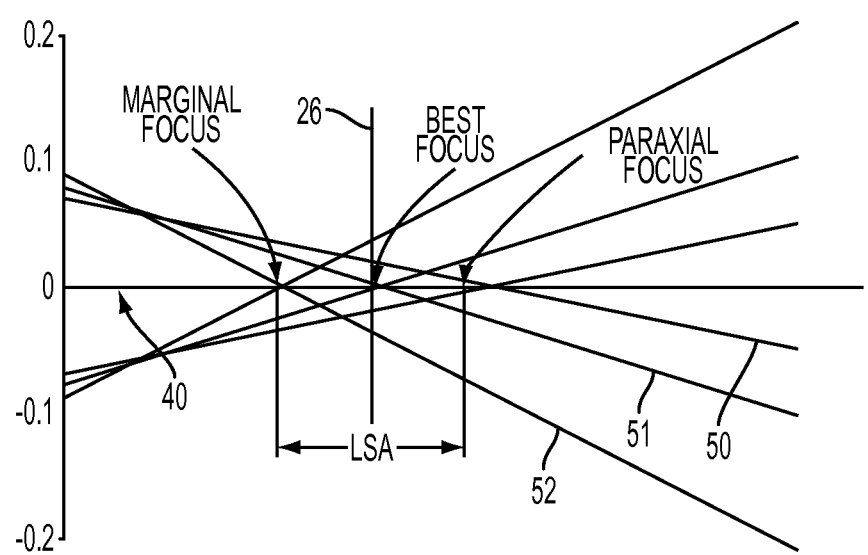
FIG. 2 is a magnified view of the retinal region of the graphical representation shown in FIG. 1.

Referring now to FIG. 2, shown is a magnified view of the region around retina 26, illustrating that rays 50, 51, 52 may come to focus at different points along optical axis 28. These points of focus are labeled as marginal focus, best focus, and paraxial focus. As illustrated, the distance between the marginal focus and the paraxial focus may be used to define a longitudinal spherical aberration (LSA). A LSA may result, for example, when the surfaces of IOL 30 are spherical, and/or due to native spherical aberration of the eye, such as a corneal spherical aberration (SA). Alternatively, one or more of the surfaces of IOL 30 may comprise an aspheric profile that is configured to reduce or to optimize or to eliminate the spherical aberrations produced by IOL 30 or by portions of eye 20, such as the aforementioned SA produced by cornea 22.

The present invention may be used in conjunction with model eye 20 to select the characteristics of IOL 30 to be implanted into a subject eye or a class of subject eyes. For example, a class of subject eyes may include subjects of a particular age group or condition (e.g., a class of subjects who have had lasik or a similar procedure). In certain embodiments, measurements from a subject eye, such as the AXL, ACD, SA, CR and/or LT, may be used in conjunction with statistical data and/or an analytical tool to determine the characteristics of IOL 30. The characteristics of the IOL resulting from embodiments of the invention may include the power of the IOL, the thickness of the IOL, the asphericity of the IOL, and/or the location of the IOL within the eye, for example.

The present invention provides a customizable procedure for predicting the optimum IOL characteristics of a specific IOL 30 for the eye of a particular individual. The apparatus, system and method discussed herein, in formulating the recommendation of IOL characteristics, may take into account biometric parameters of the individual patient, such as the SA and the expected or predicted post-op ACD of the subject eye. The empirical approach discussed herein illustrates that the apparatus, system and method of the present invention are robust for average patients, as well as for non-average patients having most levels of SA and most variations in ACD. Such non-average patients may be and include, for example, post-lasik patients.

Figure 3:
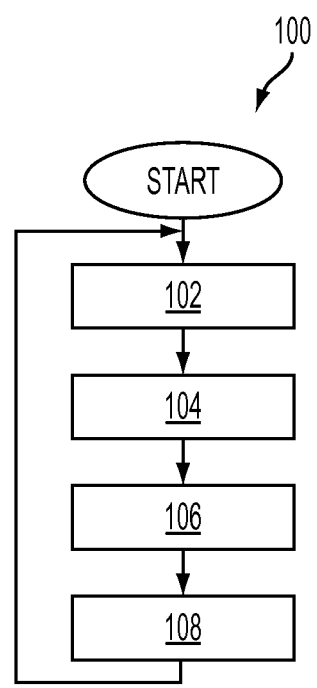
FIG. 3 is a flow chart illustrating a method of selecting an IOL according to exemplary embodiments of the invention.

More particularly, in the present invention the residual spherical aberration in the aphakic eye may be calculated empirically and/or by simulation, such as based on a number of experimental design factors, and may be used to recommend one or more IOL characteristics, such as IOL spherical aberration level, IOL power or IOL placement. FIG. 3 is a flow diagram illustrating a method 100 in accordance with the present invention. Of note, the particular design of experiments in the present invention, as indicated by the steps of method 100, was developed and executed by the present inventors using the MODDE software program, although other simulations and/or experimental design programs may, of course, be used.

At step 102, the corneal spherical aberration may be measured/simulated at a particular light level, such as at a light level correspondent to a 6 millimeter pupil size, and more particularly, the distance between the cornea, the iris, and the IOL, may be predicted. Further, the anterior corneal radius may be measured/simulated. Specifically, in the simulated data at step 102 for the experimental design of the present invention, the distance between the iris plane and the IOL was held constant at 0.9 millimeters for all cases, and the cornea to iris distance was varied between 2.1 millimeters and 4.1 millimeters. Of note, the population average ACD of 3.15 millimeters was used for the TECNIS Lens design.

For example, at step 102, a representation of the corneal topography, in the form of at least the corneal curvature or curvatures, and the pre- and/or post-operative ACD may be obtained using analytical tools known to those skilled in the art.

For the data accumulated at step 102, step 104 of method 100 calculates the spherical aberration at the iris plane. More particularly, step 104 may calculate the spherical aberration for a given range of pupils at the iris plane, such as at a 5 millimeter and 5.3 millimeter pupil. Table 1 illustrates exemplary results for this step 104 for the designed experiment of the present invention using OSLO simulation program.

TABLE 1

| SA cornea(μm) 6 mm pupil | ACD (mm) | Anterior Corneal Radius(mm) | SA(μm) 5.3 mm Iris Pupil | SA(μm) 5.0 mm Iris Pupil |
|---|---|---|---|---|
| 0.12 | 3 | 7 | 0.110 | 0.087 |
| 0.39 | 3 | 7 | 0.351 | 0.278 |
| 0.12 | 5 | 7 | 0.153 | 0.121 |
| 0.39 | 5 | 7 | 0.492 | 0.390 |
| 0.12 | 3 | 8.5 | 0.100 | 0.079 |
| 0.39 | 3 | 8.5 | 0.324 | 0.256 |
| 0.12 | 5 | 8.5 | 0.129 | 0.102 |
| 0.39 | 5 | 8.5 | 0.421 | 0.333 |
| 0.12 | 4 | 7.77 | 0.119 | 0.094 |
| 0.39 | 4 | 7.77 | 0.387 | 0.306 |
| 0.27 | 3 | 7.77 | 0.229 | 0.181 |
| 0.27 | 5 | 7.77 | 0.307 | 0.243 |
| 0.27 | 4 | 7 | 0.283 | 0.225 |
| 0.27 | 4 | 8.5 | 0.251 | 0.199 |
| 0.27 | 4 | 7.77 | 0.264 | 0.209 |

As illustrated in Table 1, the corneal spherical aberration at a 6 millimeter pupil was varied as per the distribution for a typical cataract population. Likewise, the anterior chamber depth in millimeters was varied as per the distribution for a typical cataract population. Additionally, the corneal strength, referred to in Table 1 as the Anterior Corneal Radius in Millimeters, was also varied. Table 1 illustrates, based on these factors, the calculation of spherical aberration (in micrometers) at the iris plane at the referenced 5 and 5.3 millimeter pupil.

The accumulation and/or simulation of data at step 104 may then be employed to develop a regression formula at step 106. In particularly preferred embodiments of the present invention, the regression at step 106 may account for at least one of corneal spherical aberration and ACD, and may further account for other factors, such as corneal power, for example. The regression may empirically indicate constant values for association with each such variable factor accounted for in the regression, and may reflect the empirical and/or simulated findings for the spherical aberration at the iris plane at step 104.

Step 108 may use the regression calculation of step 106 in a calculation of a customized recommendation of one or more IOL characteristics. Step 108 may include, for example, determining a desired postoperative condition, such as a postoperative refraction and/or spherical aberration, and calculating IOL characteristics such that the desired postoperative condition is achieved. The desired refractive outcome may be, for example, improved distance vision and/or near vision, such as providing the patient with sufficient visual acuity to eliminate the need for external corrective spectacles or contact lenses for near and/or distant vision.

The expected postoperative conditions may be used to compute the IOL characteristics by means, for example, of an analytical tool (e.g., a regression routine) employing the empirical regression outcome from step 106, and/or by means of using the empirical outcome of step 106 in a secondary regression. For example, the patient eye may be simulated in a regression step 108 that includes, as a characteristic of the modeled patient eye, the empirical outcome of spherical aberration at the iris plane gained at step 106. Such a regression may allow for the calculation of different optical quality parameters from which the modulation transfer function (MTF) can be retrieved. The area under the MTF may then be used to assess whether the desired postoperative condition(s) is met by the modeled IOL of step 108.

Alternatively, at step 108, a classical regression calculation may be modified by the regression outcome for spherical aberration at the iris plane derived at step 106. More particularly, using the data from step 102, a regression analysis may be performed, based on pre-operative data and the regression outcome of step 106, to provide the recommended IOL characteristics at step 108, such as the optimum IOL power.

Method 100 thus accounts for the non-constant nature of SA and ACD in a broader population of surgical subjects. As such, method 100 is applicable to average eyes, as that term is defined above, and to non-average eyes, such as eyes having significant variations from the average range in SA and/or ACD.

Figure 4:
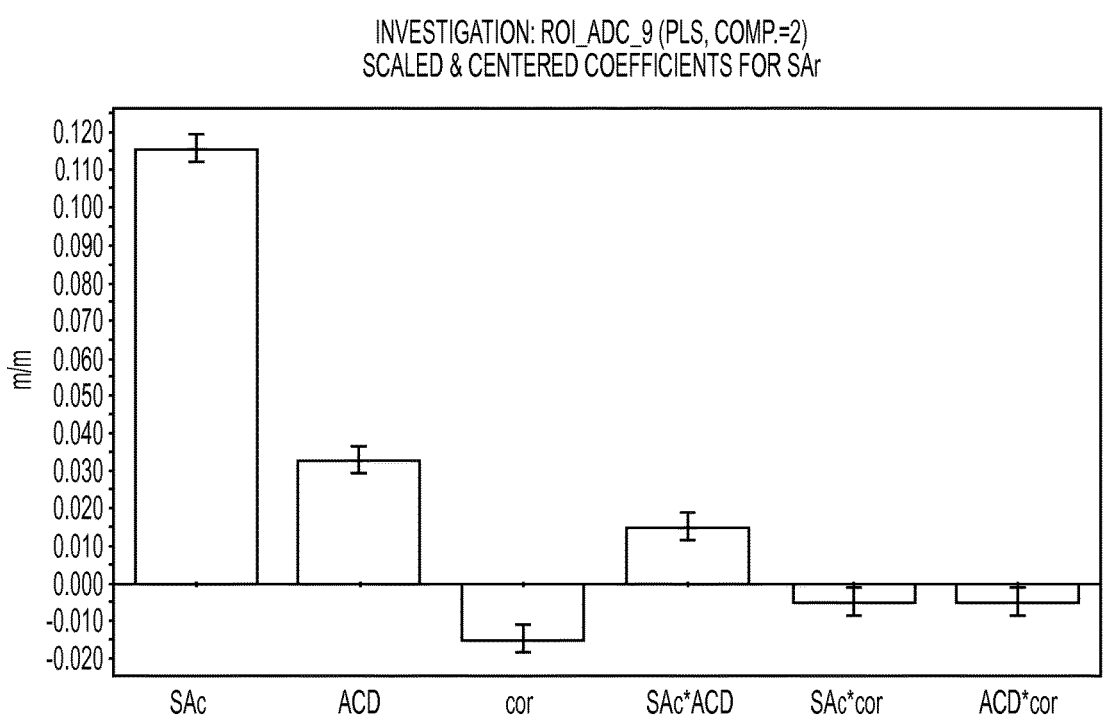
FIG. 4 is a bar diagram illustrating, based on an execution of method 100 using the MODDE design of experiments, the significance of certain factors in the spherical aberration response at the iris.

FIG. 4 is a bar diagram illustrating, based on an execution of method 100 using the aforementioned MODDE design of experiments, the significance of certain factors in the spherical aberration response at the iris. That is, FIG. 4 illustrates the importance of particular factors in a regression formula predicting spherical aberration at the iris plane. The factors included in FIG. 4 are the SA, the ACD, the corneal strength, the SA crossed with the ACD, the SA crossed with the corneal strength, and the ACD crossed with the corneal strength.

FIG. 4 illustrates that the corneal SA and the expected post-operative ACD are the most important factors in influencing the residual aphakic spherical aberration at the pupil plane. As such, the design of experiments discussed in Table 1, in conjunction with certain of the results illustrated in FIG. 4, may be used to develop the regression, at step 106, that is predictive of the aphakic spherical aberration at the pupil plane. That regression equation, including the factors referenced above, namely the corneal power, the SA, the expected post-operative ACD, and the cross terms, is:

$$SA_r = -0.285451 + 1.00614 * SA_c + 0.0742716 * ACD + 0.0371122 * cor + 0.153398 * SA_c * ACD - 0.0788237 * SA_c * cor - 0.00967978 * cor * ACD \quad \text{[EQUATION 1]}$$

where $SA_r$ is the spherical aberration at the iris plane, $SA_c$ is the corneal SA, and cor is the anterior corneal radius.

Figure 5:
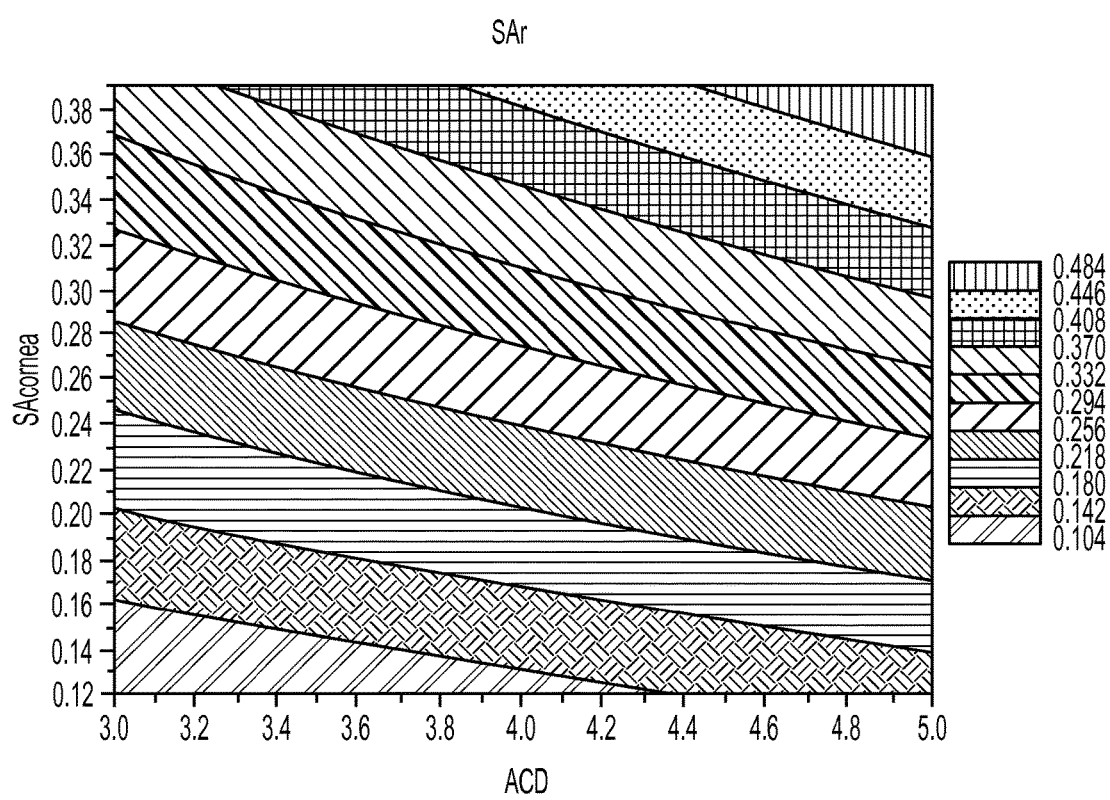
FIG. 5 is a graphical illustration of the predicted aphakic spherical aberration at the iris plane for a pupil of 5.3 millimeters and an anterior corneal radius of 7 millimeters for different levels of corneal spherical aberration and different post-op ACD distances present in a cataract population.

FIG. 5 is a graphical illustration of the predicted aphakic spherical aberration at the iris plane for a pupil of 5.3 millimeters and an anterior corneal radius of 7 millimeters. More particularly, FIG. 5 illustrates the outcome of the spherical aberration at the iris plane for the association of the constants in EQUATION 1 with the variable inputs shown in FIG. 5.

Figure 6:
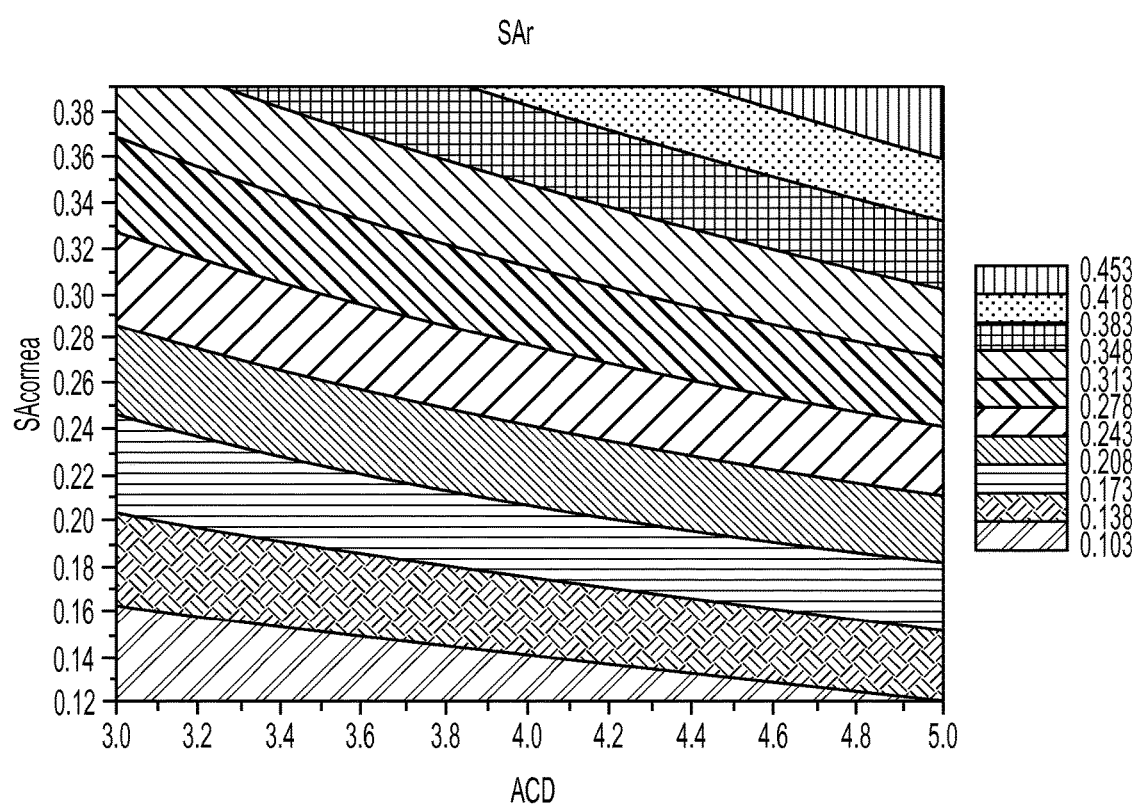
FIG. 6 graphically illustrates the predicted aphakic spherical aberration at the iris plane for a pupil of 5.3 millimeters and an anterior corneal radius of 7.77 millimeters for different levels of corneal spherical aberration and different post-op ACD distances present in a cataract population.

Similarly, FIG. 6 graphically illustrates the predicted aphakic spherical aberration at the iris plane for a pupil of 5.3 millimeters and an anterior corneal radius of 7.77 millimeters. Of note, the TECNIS Lens, for example, is designed for a SA of 0.27 micrometers and an ACD of 4 millimeters. Thus, the design parameters from EQUATION 1 may provide, such as in the exemplary embodiment shown in FIG. 6, a lens customized to address spherical aberration at the iris plane over a significantly greater percentage of population variations, in SA and ACD, than is provided by the prior art.

Figure 7:
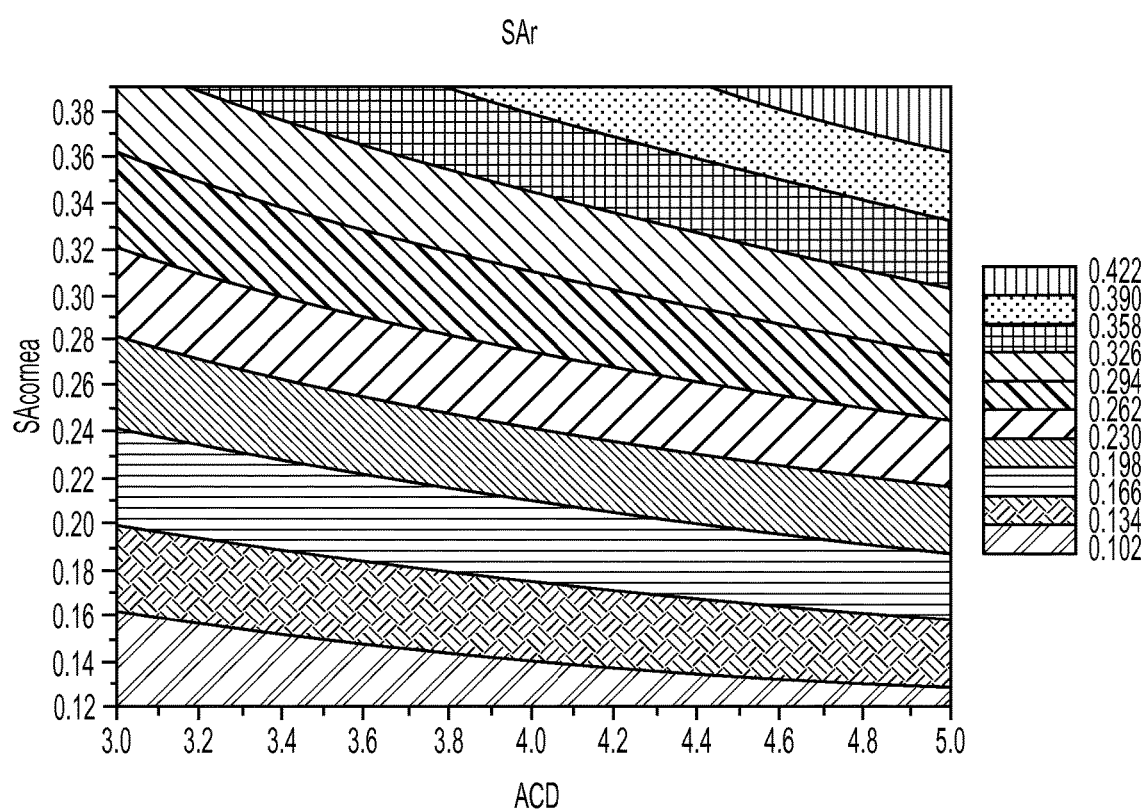
FIG. 7 illustrates the predicted aphakic spherical aberration at the iris plane for a pupil of 5.3 millimeters and an anterior corneal radius of 8.5 millimeters for different levels of corneal spherical aberration and different post-op ACD distances present in a cataract population.

FIG. 7 illustrates the predicted aphakic spherical aberration at the iris plane for a pupil of 5.3 millimeters and an anterior corneal radius of 8.5 millimeters. FIG. 7 again illustrates the accounting, by EQUATION 1, for a number of factors affecting the spherical aberration at the iris plane not accounted for in prior art methods.

FIGS. 5 through 7 illustrate that an IOL design for the average population, with respect to at least SA and ACD, is unlikely to provide the expected visual outcome over a population of patients having significant variations from the average SA and ACD. This undesirable outcome occurs because prior lens designs cannot drive post-operative spherical aberration at the iris plane to 0 or near 0, due at least to the dependency of post-operative spherical aberration at the iris plane on the pre-operative SA and the post-operative ACD. More particularly, spherical aberration at the iris plane cannot be driven towards 0 or near 0 for patients having SA and ACD outside the average using the prior art solutions, because prior art lens designs account only for the average data with respect to these variables.

Thus, unlike the prior art, method 100 provides customized treatment for eyes matching different, non-average eye model parameters. For example, in accordance with EQUATION 1, eyes with a large ACD typically correlate negatively with corneal radius. The present invention has applied IOLs designed using method 100 to three customized eye models, namely the TECNIS lens eye model for the average eye, an eye having a large iris to cornea distance, a high corneal spherical aberration and a high corneal power, and an eye having a small iris to cornea distance, a low spherical aberration and a low corneal power.

Table 2 provides the inputs for the design of three IOLs, using the variables listed including the TECNIS lens design. The IOL designs compensate fully for the spherical aberration. Of course, it goes without saying that other subdivisions and combinations of variable inputs may be used for lens designs using equation 1 which output the aphakic spherical aberration at the pupil plane ranging from 0.079 μm to 0.390 μm for 5 mm pupil for the variables listed. These outputs may be used to design IOLs with a SA to optimize ocular SA outcomes. Using the residual SA at the pupil plane or predicted IOL plane, an optimal SA value of the IOL may be designed and selected to obtain the targeted ocular SA.

TABLE 2

| IOL Design | Anterior Corneal radius (mm) | Cornea-iris Distance (mm) | Corneal spherical aberration 6 mm pupil (μm) | Conical constant |
|---|---|---|---|---|
| L_L | 8.5 | 2.1 | 0.12 | −0.4 |
| TECNIS | 7.77 | 3.1 | 0.27 | −0.18 |
| H_H | 7 | 4.1 | 0.39 | 0 |

Figure 8:
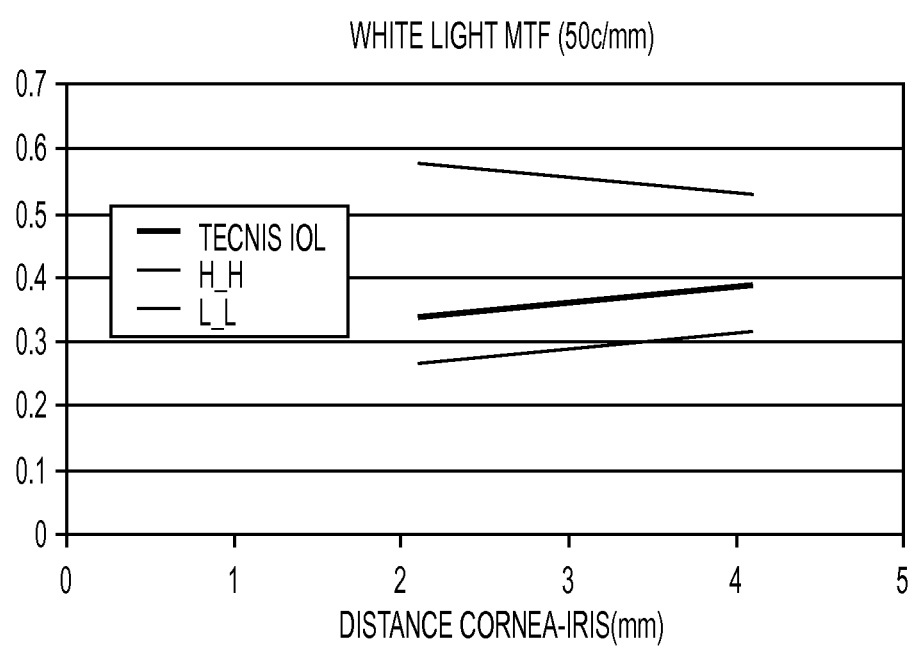
FIG. 8 is a graphical illustration for three different IOLs with different levels of spherical aberration result in different best focus modulation transfer function results obtained with the present invention for an eye having a corneal spherical aberration of 0.17 µm for a 6 mm corneal aperture.
Figure 9:
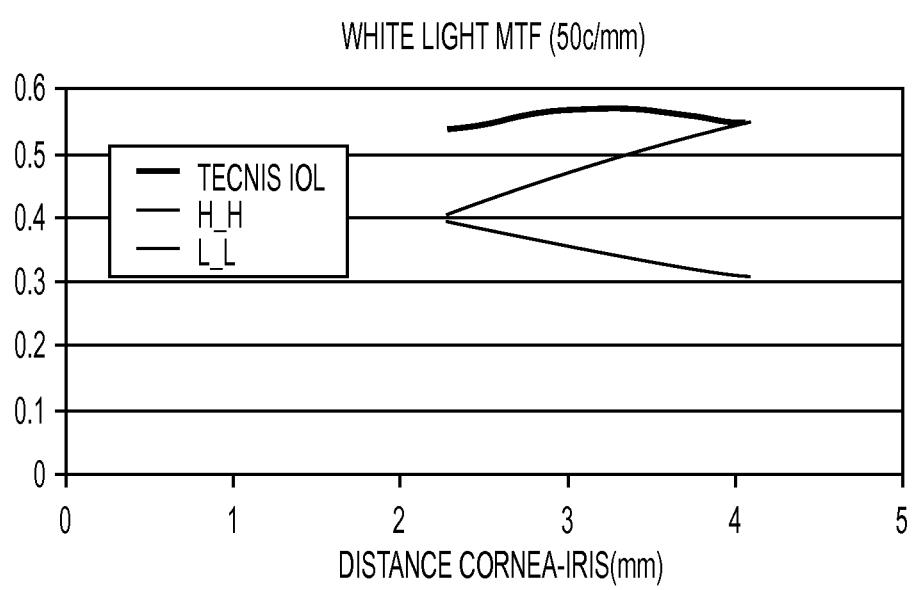
FIG. 9 is a graphical illustration for three different IOLs with different levels of spherical aberration result in different best focus modulation transfer function results obtained with the present invention for an eye having a corneal spherical aberration of 0.27 µm for a 6 mm corneal aperture.
Figure 10:
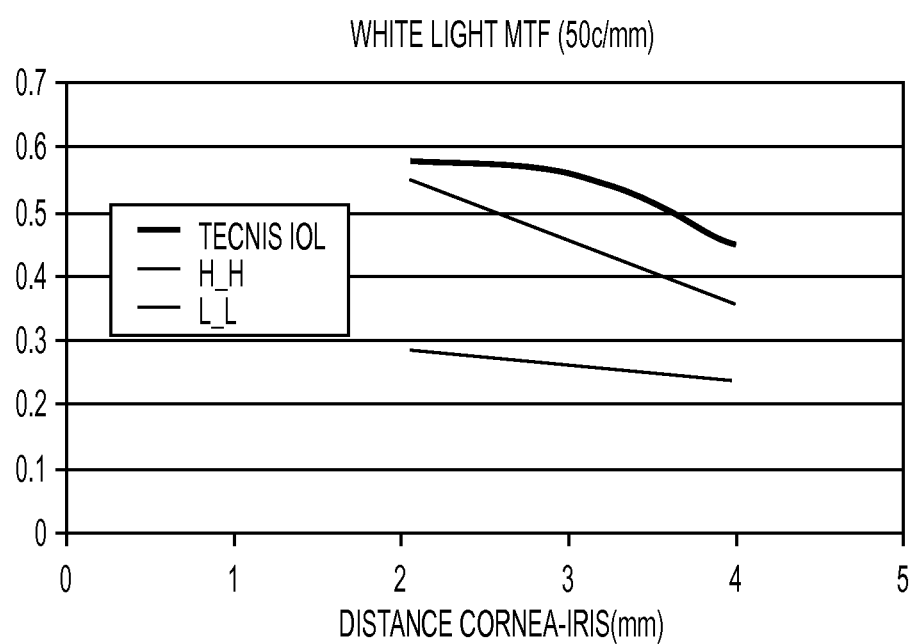
FIG. 10 is a graphical illustration for three different IOLs with different levels of spherical aberration result in different best focus modulation transfer function results obtained with the present invention for an eye having a corneal spherical aberration of 0.39 µm for a 6 mm corneal aperture.

The three exemplary lens designs set forth in Table 2, with 20 diopters of optical power, were tested using the white light modulation transfer function (50 c/millimeter) and a plurality of eye models having average corneal power (anterior radius of 7.77 millimeters) and a 5 millimeter pupil. In accordance with these tests, the SA and the ACD were varied. The results of this testing are provided in FIGS. 8, 9 and 10, at SA of 0.12 micrometers, 0.27 micrometers, and 0.39 micrometers, respectively. The results of FIGS. 8-10 demonstrate that best-focus MTF results may be obtained with the present invention, thus indicating that spherical aberration at the iris plane may be minimized, for realistic amounts of ACD and SA, across a broader population of eyes than was treatable to obtain best-focus MTF in the prior art.

Of course, and as referenced above, various combinations may be provided, such as lower or higher corneal power, in combination with other factors, other than those graphically shown in the exemplary illustrations herein. In such circumstances, EQUATION 1 and method 100 still provide improved meeting of expected MTF behavior for the lens under design, i.e. method 100 better provides the expected improved visual results. In light of this expectation of improved visual performance, a surgeon may, in accordance with the present invention, select an IOL meeting the conditions of step 108 of method 100, wherein the selected IOL is appropriate for the patient based on an expected aphakic spherical aberration as indicated by EQUATION 1.

Those skilled in the art will appreciate, in light of the discussion herein, that other criteria may be incorporated to obtain the desired visual outcome, and that the present invention may be applied in circumstances of non-typical IOLs and other eye treatments. For example, depth of focus may be included as a criteria for the desired visual outcome, and may be balanced with a best focus design parameter. Likewise, terms may be included to account for other variables such as, for example, LHP or predicted postoperative vitreous length, other aberrations, or the like. Further, in addition to typical IOLs, the present invention may be employed with multifocal IOLs, basic procedures, glasses and contact lenses, by way of non-limiting example.

Figure 11:
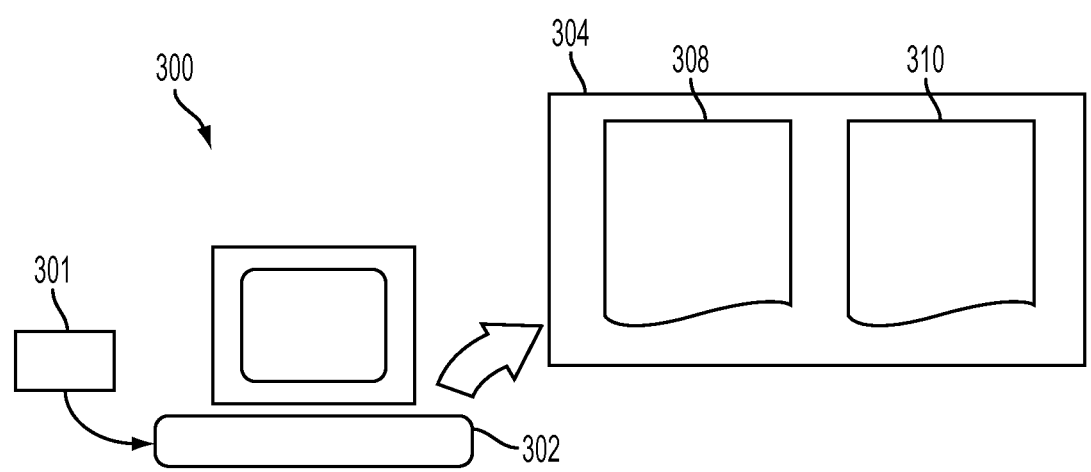
FIG. 11 is a block diagram illustrating the implementation of the present invention in a clinical system.

FIG. 11 is a block diagram illustrating the implementation of the present invention in a clinical system 300 comprised of one or more apparatuses that are capable of assessing the eye's biometry and of performing the calculations and comparisons set forth in method 100. The system 300 may include a biometric reader and/or biometric simulation input 301, a processor 302, and a computer readable memory 304 coupled to the processor 302. The computer readable memory 304 includes therein an array of ordered values 308 and sequences of instructions 310 which, when executed by the processor 302, cause the processor 302 to select an implantable IOL configured for implantation into the eye of the subject presenting the biometric readings to biometric reader 301. The array of ordered values 308 may comprise data used or obtained from method 100 or other methods consistent with embodiments of the invention. For example, the array of ordered values 308 may comprise one or more desired refractive outcomes, parameters of an eye model based on one or more characteristics of at least one eye, and data related to characteristics of an IOL or set of IOLs, such as optical power, an aspheric profile, and/or a lens plane.

The sequence of instructions 310 may include one or more steps of method 100 or other methods consistent with embodiments of the invention. In some embodiments, the sequence of instructions 310 includes applying the custom regression of method 100 and EQUATION 1, performing one or more calculations to determine a predicted refractive outcome based on an eye model, a regression algorithm, comparing a predicted refractive outcome to a desired refractive outcome, and based on the comparison, repeating the calculation with an IOL having at least one of a different power, a different aspheric profile, and a different lens plane.

The processor 302 may be embodied in a general purpose desktop or laptop computer, and/or may comprise hardware associated with biometric reader 301 specifically for selecting an IOL for placement into the eye of the subject. In certain embodiments, the system 300 may be configured to be electronically coupled to another device, such as one or more instruments for obtaining measurements of an eye or a plurality of eyes in conjunction with, or in addition to, biometric reader 301. Alternatively, the system 300 may be embodied in a handheld device that may be adapted to be electronically and/or wirelessly coupled to one or more other devices.

Additional studies were conducted to predict ocular spherical aberration, where simulations were performed using a realistic eye model. The eye model exhibits the average corneal SA and chromatic aberration found in a population of cataract patients. Published clinical data on variations in corneal geometry and a 2 mm range in intraocular lens position were input into the model. A predictive model using different ocular geometry was built from the simulations.

The spherical aberration was calculated in the aphakic eye model at the pupil plane (5.3 mm) varying as follows: anterior corneal radius: 7 mm-8.5 mm; corneal SAc 6 mm: 0.12 μm-0.39 μm; Cornea-pupil distance PP: 2.1 mm-4.1 mm. PP is equal to the ACD as defined before minus 0.9 mm.

Figure 12:
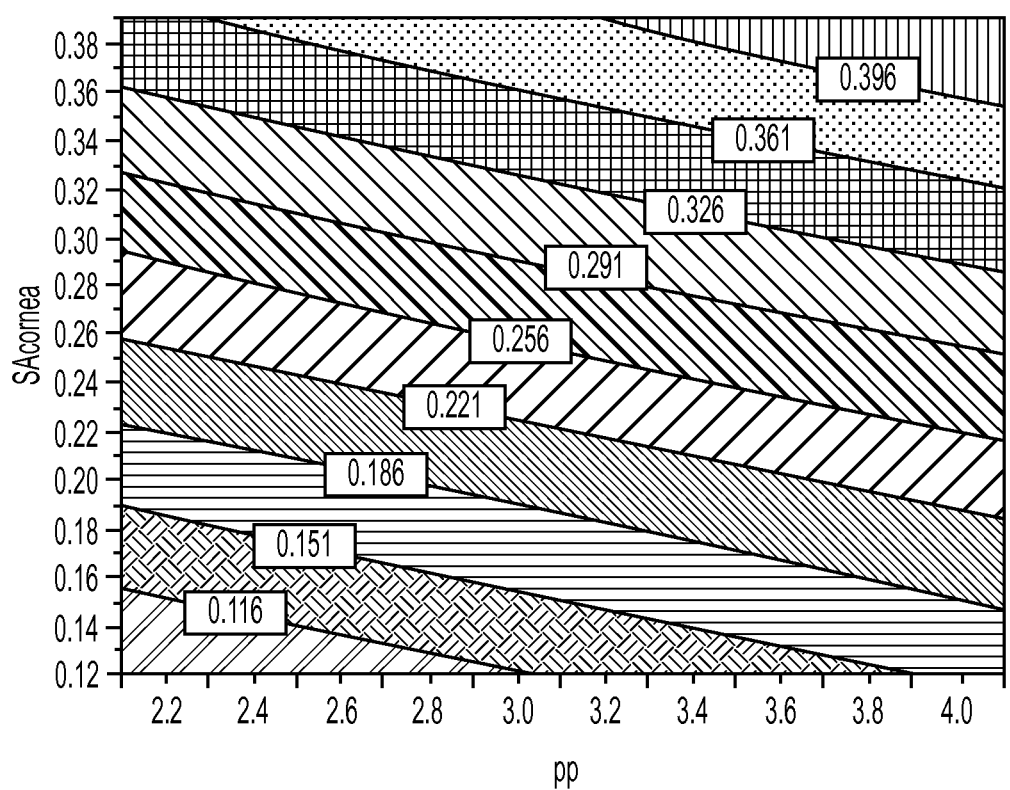
FIG. 12 illustrates the dependence of spherical aberration with corneal spherical aberration (6 mm) and pupil plane.

The simulations resulted in a quadratic predictive model, with a high degree of correlation (R2=0.96) showing that the propagated SA strongly depends on corneal SAc and position of pupil plane, but not on corneal power. FIG. 12 illustrates the dependence of propagated spherical aberration with corneal spherical aberration (6 mm) and pupil plane. The regression equation for SA at the pupil plane is:

$$SA = 0.054833 - 0.02816*PP + 0.004457PP^2 + 0.395401*Sac + 0.274583*SAc^2 + 0.152815*PP*SAc \quad [\text{EQUATION 2}]$$

The prediction of true lens position and measured postoperative corneal spherical aberration was used to calculate the ocular spherical aberration using model illustrated in FIG. 12, above. The true lens position is defined at the position of the posterior vertex of the IOL. The distance PP may now be calculated from the true lens position by adding the center thickness of IOL and 0.9 mm.

Figure 13:
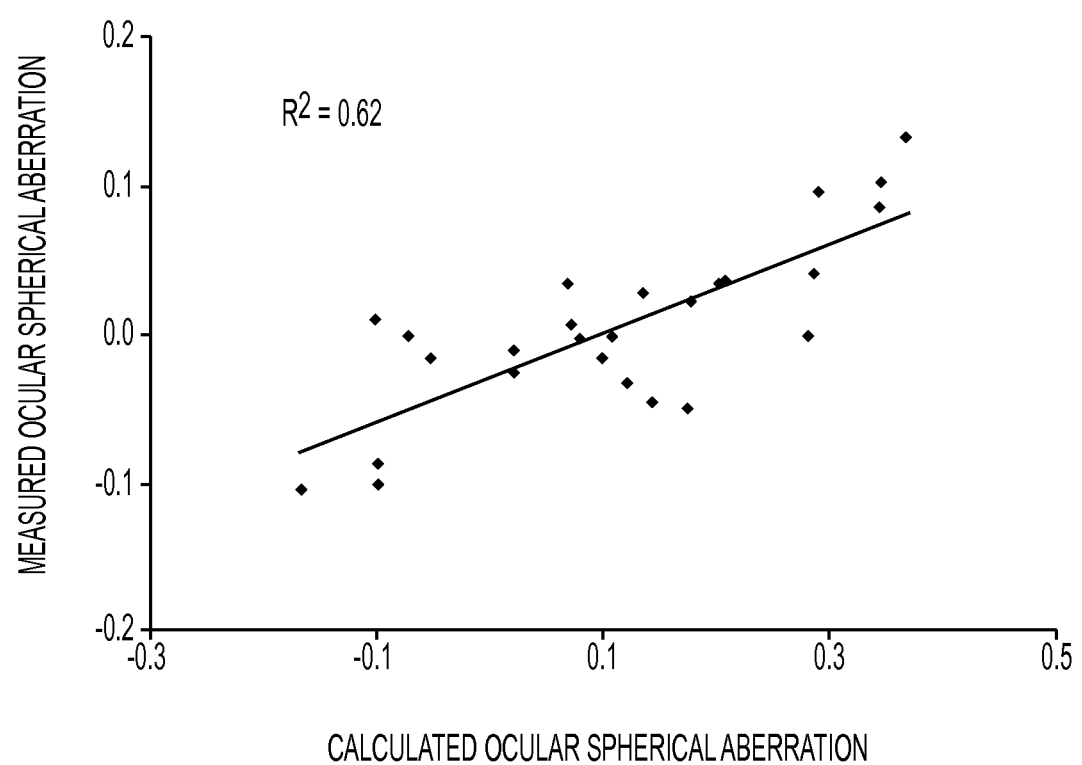
FIG. 13 is a graph illustrating $R^2$ for measured ocular spherical aberration versus calculated ocular spherical aberration.

The correlation between calculated and measured ocular spherical aberration didn't improve when the measured true lens position was introduced. The calculated ocular spherical aberration is the predicted value from the regression formula (i.e., EQUATION 2) added with the SA of the IOL. See FIG. 13.

Those of ordinary skill in the art may recognize that many modifications and variations of the present invention may be implemented without departing from the spirit or scope of the invention. Thus, it is intended that the present invention covers the modifications and variations of this invention provided they come within the scope of the discussion herein and any appended claims, and any equivalents thereto.

What is claimed is:

1. In a biometric reader and simulation system having a processor and a non-transitory computer-readable medium containing a sequence of instructions, an electronic method executed by the processor that determines an optimum intraocular lens for a patient by simulating a postoperative condition of an eye prior to operation, said electronic method comprising:
    using the biometric reader, measuring a corneal spherical aberration of an eye;
    determining an expected post-operative anterior chamber depth of the eye;
    empirically calculating a residual aphakic spherical aberration at an iris plane of the eye, based on a regression formula comprising at least the measured corneal spherical aberration and the expected post-operative anterior chamber depth, and cross products thereof;
    predictively estimating, in accordance with an output of said empirically calculating step, at least one of a spherical aberration level, a power, and a thickness of an intraocular lens that will obtain a desired postoperative condition of the eye when surgically implanted in the eye; and
    selecting an intraocular lens in accordance with the at least one of the predictive estimations.

2. The method of claim 1 further comprising measuring at least one of axial length, corneal power, preoperative anterior chamber depth, and preoperative lens thickness.

3. The method of claim 1, wherein the desired postoperative condition comprises a postoperative spherical aberration.

4. The method of claim 1, wherein measuring a corneal spherical aberration comprises obtaining a corneal topography.

* * * * *